United States Patent
Nam et al.

(10) Patent No.: US 11,442,254 B2
(45) Date of Patent: Sep. 13, 2022

(54) AUGMENTED REALITY PROJECTION DEVICE

(71) Applicant: INNER RAY, INC., San Ramon, CA (US)

(72) Inventors: Dong Wook Nam, San Ramon, CA (US); Joo Hyung Hong, Suwon-si (KR)

(73) Assignee: Inner Ray, Inc., San Ramon, CA (US)

( * ) Notice: Subject to any disclaimer, the term of this patent is extended or adjusted under 35 U.S.C. 154(b) by 831 days.

(21) Appl. No.: 16/377,060

(22) Filed: Apr. 5, 2019

(65) Prior Publication Data
US 2020/0319431 A1 Oct. 8, 2020

(51) Int. Cl.
*G02B 13/00* (2006.01)
*G02B 13/22* (2006.01)

(52) U.S. Cl.
CPC .......... *G02B 13/0095* (2013.01); *G02B 13/22* (2013.01)

(58) Field of Classification Search
CPC .... G02B 13/0095; G02B 13/22; G02B 13/16; G02B 26/0833; G02B 27/1006; G02B 27/141; G02B 27/20; A61B 2090/365; A61B 2090/366; A61B 90/37; A61B 2090/376; G03B 35/26; G03B 21/006
USPC ........................................................ 359/434
See application file for complete search history.

(56) References Cited

U.S. PATENT DOCUMENTS

| 5,283,736 | A | * | 2/1994 | Nagatsuka | G06T 7/136 |
| | | | | | 382/172 |
| 6,366,383 | B1 | | 4/2002 | Roeder | |
| 7,289,277 | B2 | | 10/2007 | Ryzhikov et al. | |
| 7,317,578 | B2 | | 1/2008 | Drazic et al. | |
| 7,996,068 | B2 | | 8/2011 | Telischak et al. | |
| 9,188,767 | B2 | | 11/2015 | Ito et al. | |
| 9,743,836 | B2 | | 8/2017 | Tsubouchi et al. | |
| 2009/0140170 | A1 | * | 6/2009 | Nevill | G01N 21/6428 |
| | | | | | 250/459.1 |
| 2009/0289200 | A1 | | 11/2009 | Ishii | |
| 2011/0125028 | A1 | | 5/2011 | Wood et al. | |

(Continued)

FOREIGN PATENT DOCUMENTS

| JP | 2003-111716 | 4/2003 |
| JP | 3487933 | 10/2003 |

(Continued)

*Primary Examiner* — Stephone B Allen
*Assistant Examiner* — Rahman Abdur
(74) *Attorney, Agent, or Firm* — Knobbe Martens Olson & Bear LLP

(57) ABSTRACT

An augmented reality projection device is provided. The augmented reality projection device includes an excitation light source that generates excitation light and a fluorescent light detector that detects fluorescent light generated in the fluorescent light generation area and generates a fluorescent image. The device also includes a projector that converts an image signal for displaying a visual indicator in the fluorescent light generation area into visual indicator light. The device further includes a processor that controls operations of the excitation light source, the fluorescent light detector, and the projection. The device further includes a coaxial optics that delivers the excitation light and the visual indicator light to the fluorescent light generation area and delivers the fluorescent light to the fluorescent light detector.

16 Claims, 10 Drawing Sheets

(56) References Cited

U.S. PATENT DOCUMENTS

| | | |
|---|---|---|
| 2012/0259231 A1* | 10/2012 | Tsubouchi ........... A61B 5/0071 600/477 |
| 2017/0079741 A1 | 3/2017 | Makinouchi |
| 2018/0000330 A1 | 1/2018 | Takeuchi et al. |
| 2018/0042692 A1 | 2/2018 | Kim et al. |

FOREIGN PATENT DOCUMENTS

| | | |
|---|---|---|
| JP | 3568280 | 6/2004 |
| JP | 2006-102360 | 4/2006 |
| JP | 2006-180926 | 7/2006 |
| JP | 5623266 | 10/2014 |
| JP | 5915949 | 4/2016 |
| JP | 6152951 | 6/2017 |
| KR | 10-1784063 | 10/2017 |
| KR | 10-1784970 | 10/2017 |
| KR | 10-2018-0006668 | 4/2018 |
| WO | WO 2009/052466 | 4/2009 |
| WO | WO 2012/003127 | 1/2012 |
| WO | WO 2015/103420 | 7/2015 |

\* cited by examiner

AUGMENTED REALITY PROJECTION DEVICE

FIELD

The described technology generally relates to an augmented reality projection device.

DESCRIPTION OF THE RELATED TECHNOLOGY

A fluorescent material which is administered into a human body can be used to identify a lesion. A lesion can be easily distinguished from surrounding normal tissues by fluorescent light. When excitation light of a specific wavelength is applied, a fluorescent material emits light of a wavelength other than that of excitation light, that is, fluorescent light. Although it depends on a type of a fluorescent material, light of a long wavelength, for example, red or near-infrared light, is used as excitation light. Since brightness of fluorescent light is relatively weak in comparison with excitation light or ambient light and, particularly, the wavelength of fluorescent light belongs to a band other than visible light, an operator cannot easily recognize fluorescent light. In order to complement this, an operator can ascertain a lesion while watching a monitor on which an image captured by a fluorescent camera is displayed. However, since an image displayed on the monitor is merely an aid, an operator has to perform a surgical operation while alternately watching an incised area and the monitor.

SUMMARY

In general aspect, an augmented reality projection device can include an excitation light source that generates excitation light which is applied to a fluorescent light generation area to excite a fluorescent material, a fluorescent light detector that detects fluorescent light generated in the fluorescent light generation area and generates a fluorescent image, the fluorescent light including a fluorescent light detection area corresponding to the fluorescent light generation area, a projector that converts an image signal for displaying a visual indicator in the fluorescent light generation area into visual indicator light, the visual indicator being generated to correspond to the identified fluorescent light detection area, a processor that controls operations of the excitation light source, the fluorescent light detector, and the projection, and a coaxial optics that delivers the excitation light and the visual indicator light to the fluorescent light generation area and delivers the fluorescent light to the fluorescent light detector, wherein the excitation light, the fluorescent light, and the visual indicator light pass through optical paths which are partially common by the coaxial optics.

Implementations of the augmented reality projection device in general aspect can include one or more of the following features.

The coaxial optics can include an optical path branching/merging unit that causes an optical path of the excitation light and an optical path of the visual indicator light to be substantially identical to each other and substantially branches an optical path of the fluorescent light from the optical path of the excitation light, a relay optics that delivers the excitation light, the fluorescent light, and the visual indicator light in processing directions thereof, a half pentaprism that is horizontally coupled to the relay optics, inclines the optical path of the excitation light and the optical path of the visual indicator light, and causes the optical path of the fluorescent light to be horizontal, and an objective optics that is obliquely coupled to the half pentaprism and is configured to deliver the excitation light and the visual indicator light emitted from the half pentaprism to the fluorescent light generation area and to deliver the fluorescent light emitted from the fluorescent light generation area to the half pentaprism.

The optical path branching/merging unit can include a first dichroic mirror that is disposed oblique at a position at which the excitation light emitted from the excitation light source and progressing horizontally and the fluorescent light progressing vertically to the fluorescent light detector intersect each other and is configured to reflect the excitation light and to transmit the fluorescent light, and a second dichroic mirror that is disposed oblique at a position at which the visual indicator light emitted from the projector and progressing horizontally and the excitation light reflected by the first dichroic mirror and progressing vertically intersect each other and is configured to reflect the excitation light and the fluorescent light and to transmit the visual indicator light.

The augmented reality projection device can further include an image sensor that generates a color signal using visible light which is reflected from the fluorescent light generation area to which a visual indicator has been projected using the visual indicator light, and a third dichroic mirror that is disposed oblique between the second dichroic mirror and the projector and is configured to transmit the visual indicator light and to reflect the visible light, wherein the visible light reaches the image sensor through the coaxial optics.

The first dichroic mirror and the third dichroic mirror can be disposed to be substantially parallel to each other and the first dichroic mirror and the second dichroic mirror are disposed to be perpendicular to teach other.

A resolution of the fluorescent light detector can be equal to or less than a resolution of the image sensor.

The optical path branching/merging unit can include a first dichroic mirror that is disposed oblique at a position at which the excitation light emitted from the excitation light source and progressing horizontally and the fluorescent light progressing vertically intersect each other and is configured to transmit the excitation light and to reflect the fluorescent light, and a second dichroic mirror that is disposed oblique at a position at which the visual indicator light emitted from the projector and progressing horizontally and the excitation light transmitted by the first dichroic mirror intersect each other and is configured to reflect the excitation light and the fluorescent light and to transmit the visual indicator light.

Brightness of the visual indicator can reflect brightness of the fluorescent light.

The visual indicator light can be monochromatic light.

The coaxial optics can include an optical path branching/merging unit that causes an optical path of the excitation light and an optical path of the visual indicator light to be substantially identical to each other and substantially branches an optical path of the fluorescent light from the optical path of the excitation light, a relay optics that delivers the excitation light, the fluorescent light, and the visual indicator light in processing directions thereof, and an objective optics that is obliquely coupled to the relay optics and is configured to deliver the excitation light and the visual indicator light emitted from the relay optics to the fluorescent light generation area and to deliver the fluorescent light emitted from the fluorescent light generation area to the relay optics.

The augmented reality projection device can include an I/O interface that communicates with the outside, wherein the fluorescent image is output to the outside via the I/O interface and the image signal is received from the outside via the I/O interface.

The processor can identify the fluorescent light detection area in the fluorescent image and generate the image signal for displaying the visual indicator corresponding to the identified fluorescent light detection area.

The fluorescent image can be a still image or a moving image.

The visual indicator can change when a difference between fluorescent images which are generated at different times is equal to or greater than a threshold value.

In another general aspect, an augmented reality projection device can include an excitation light source that generates excitation light which is applied to a fluorescent light generation area to excite a fluorescent material, a fluorescent light detector that detects fluorescent light generated in the fluorescent light generation area and generates a fluorescent image, the fluorescent light including a fluorescent light detection area corresponding to the fluorescent light generation area, a projector that converts an image signal for displaying a visual indicator in the fluorescent light generation area into visual indicator light, the visual indicator being generated to correspond to the identified fluorescent light detection area, an image sensor that generates a color signal using visible light which is reflected from the fluorescent light generation area to which a visual indicator has been projected using the visual indicator light, and a coaxial optics that delivers the excitation light and the visual indicator light to the fluorescent light generation area and delivers the fluorescent light to the fluorescent light detector, wherein the excitation light, the fluorescent light, and the visual indicator light pass through optical paths which are partially common by the coaxial optics.

Implementations of the augmented reality projection device in general aspect can include one or more of the following features.

The coaxial optics can include an optical path branching/merging unit that causes an optical path of the excitation light and an optical path of the visual indicator light to be substantially identical to each other and substantially branches an optical path of the fluorescent light and an optical path of the visible light from the optical path of the excitation light, a relay optics that delivers the excitation light, the fluorescent light, the visual indicator light, and the visible light in processing directions thereof, a half pentaprism that is horizontally coupled to the relay optics, inclines the optical path of the excitation light and the optical path of the visual indicator light, and causes the optical path of the fluorescent light and the optical path of the visible light to be horizontal, and an objective optics that is obliquely coupled to the half pentaprism and is configured to deliver the excitation light and the visual indicator light emitted from the half pentaprism to the fluorescent light generation area and to deliver the fluorescent light and the visible light emitted from the fluorescent light generation area to the half pentaprism.

The optical path branching/merging unit can include a first dichroic mirror that is disposed oblique at a position at which the excitation light emitted from the excitation light source and progressing horizontally and the fluorescent light progressing vertically to the fluorescent light detector intersect each other and is configured to reflect the excitation light and to transmit the fluorescent light, a second dichroic mirror that is disposed oblique at a position at which the visual indicator light emitted from the projector and progressing horizontally and the excitation light reflected by the first dichroic mirror and progressing vertically intersect each other and is configured to reflect the excitation light and the fluorescent light and to transmit the visual indicator light, and a third dichroic mirror that is disposed oblique between the second dichroic mirror and the projector and is configured to transmit the visual indicator light and to reflect the visible light.

The augmented reality projection device can further include an I/O interface that communicates with the outside, wherein the fluorescent image is output to the outside via the I/O interface and the image signal is received from the outside via the I/O interface.

The coaxial optics can include an optical path branching/merging unit that causes an optical path of the excitation light and an optical path of the visual indicator light to be substantially identical to each other and substantially branches an optical path of the fluorescent light from the optical path of the excitation light, a relay optics that delivers the excitation light, the fluorescent light, and the visual indicator light in processing directions thereof, and an objective optics that is obliquely coupled to the relay optics and is configured to deliver the excitation light and the visual indicator light emitted from the relay optics to the fluorescent light generation area and to deliver the fluorescent light emitted from the fluorescent light generation area to the relay optics.

BRIEF DESCRIPTION OF THE DRAWINGS

Hereinafter, embodiments of the described technology will be described with reference to the accompanying drawings. For the purpose of easy understanding of the described technology, the same elements will be referred to by the same reference signs. Configurations illustrated in the drawings are examples for describing the described technology, and do not restrict the scope of the described technology. Particularly, in the drawings, some elements are slightly exaggerated for the purpose of easy understanding of the described technology. Since the drawings are used to easily understand the described technology, it should be noted that widths, thicknesses, and the like of elements illustrated in the drawings might change at the time of actual implementation thereof. On the other hand, the same elements in the following detailed description of the described technology will be referred to by the same reference signs, wherein.

DETAILED DESCRIPTION OF EMBODIMENTS

The described technology can be modified and be embodied in various forms, and specific embodiments thereof will be illustrated and described below. However, the embodiments are not intended to limit the described technology, but it should be understood that the described technology includes all modifications, equivalents, and replacements belonging to the concept and the technical scope of the described technology.

Terms "first," "second," and the like can be used to describe various elements, but the elements should not be limited to the terms. The terms are used only to distinguish an element from another.

The terms used in the following description are intended to merely describe specific embodiments, but not intended to limit the described technology. An expression of the singular number includes an expression of the plural number, so long as it is clearly read differently. The terms such as "comprise", "include" and "have" are intended to indicate that features, numbers, steps, operations, elements, components, or combinations thereof used in the following description exist and it should thus be understood that the possibility of existence or addition of one or more other different features, numbers, steps, operations, elements, components, or combinations thereof is not excluded.

Hereinafter, embodiments of the described technology will be described in detail with reference to the accompanying drawings.

Figure 1:
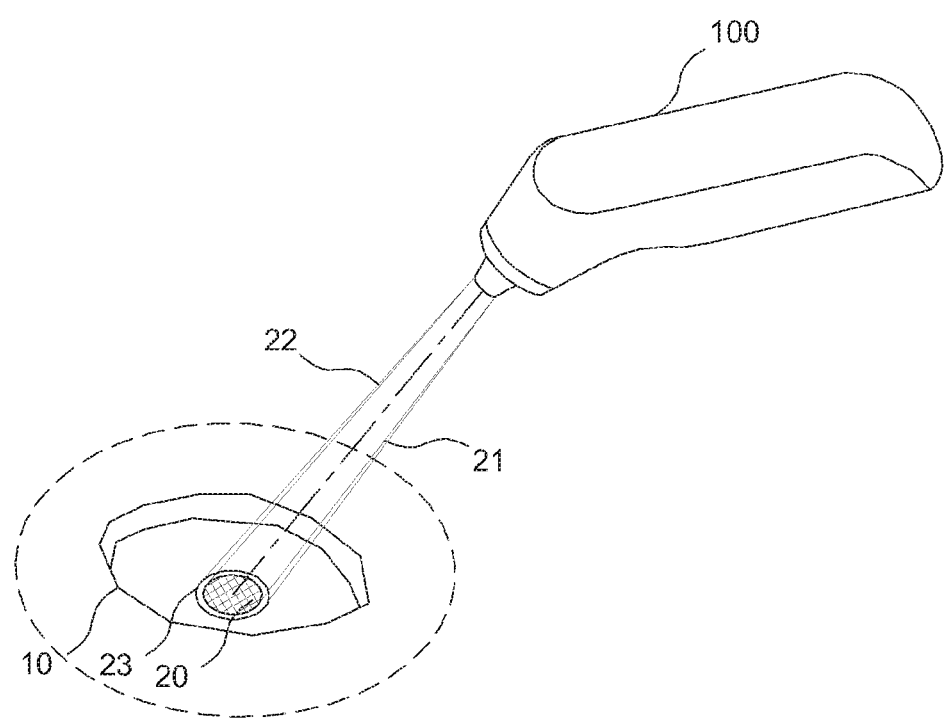
FIG. 1 is a diagram schematically illustrating a surgical operation using an augmented reality projection device.

FIG. 1 is a diagram schematically illustrating a surgical operation using an augmented reality projection device.

An augmented reality projection device 100 enables visually identifying an area which cannot be easily recognized with bare eyes. For example, the augmented reality projection device 100 can be used for a surgical operation for removing a specific area of a human body dyed with a fluorescent material. The augmented reality projection device 100 can apply fluorescence excitation light 21 to an incised area 10 and generate a visual indicator 23 for identifying an area 20 dyed with the fluorescent material at the same time or within a predetermined time. The generated visual indicator 23 can be displayed in the dyed area 20 or around the dyed area 20.

A fluorescent material is administered into a human body before a surgical operation has been started. Examples of the fluorescent material which can be administered into a human body 5-ALA (5-Aminolevulinic Acid) that emits fluorescent light which is excited with excitation light 21 of about 400 nm and has a peak at about 635 nm and ICG (indocyanine green) that emits fluorescent light which is excited with excitation light 21 of about 750 nm to about 800 nm and has a peak at about 845 nm, and the fluorescent material is not limited thereto. On the other hand, since the wavelength of fluorescent light emitted in response to the excitation light 21 does not belong to a visible band, an operator has difficulty in visually identifying fluorescent light. In an operating room, an astral light which is very bright is installed in the vicinity of an operating table and light generated from the astral light makes it more difficult to detect fluorescent light. When a wavelength of fluorescent light belongs to a band other than the visible band, an area having emitted fluorescent light can be identified by only a detector such as (near-) infrared camera. That is, an operator has to perform a surgical operation while alternately watching a monitor having an image of a dyed area 20 displayed thereon and an incised area 10. On the other hand, an incised area 20 has a red-based color mainly. Accordingly, when the color of the fluorescent light is close to red, it is very difficult to identify the dyed area 20 in the incised area 10.

The augmented reality projection device 100 includes a coaxial optics 200 (in FIG. 3) that delivers light which is generated in the augmented reality projection device 100 to the incised area 10 and delivers light which is generated or reflected by the incised area 10 to the inside of the augmented reality projection device 100. Light which is generated by the augmented reality projection device 100 can include excitation light 21 and visual indicator light 22. The excitation light 21 is light belonging to a wavelength band which is not easily recognized by an operator with bare eyes. The visual indicator light 22 is light belonging to a visible band. The visual indicator light 22 may be visible light belonging to a relatively narrow wavelength band, for example, light indicating a specific color such as green or blue. Light which is incident into the augmented reality projection device 100 can include fluorescent light generated in the dyed area 20 and visible light reflected by the incised area 10. In the augmented reality projection device 100, an optical axis of the excitation light 21, an optical axis of fluorescent light, an optical axis of the visual indicator light 22, and an optical axis of reflected visible light may at least partially match each other.

The augmented reality projection device 100 is a handheld type device which can be gripped by an operator. The size of the augmented reality projection device 100 can be decreased due to the coaxial optics 200. Light which is emitted from the augmented reality projection device 100 to an incised area 10 and light which is incident on the augmented reality projection device 100 from the incised area 10 pass through the coaxial optics 200. In a structure in which optics are separated, an optics for capturing an image and optics for projecting an image are necessarily separated from each other. Accordingly, a projected image can be distorted, and thus image processing for compensating for the distortion is necessary. Particularly, the separated optical systems hinder a decrease in size of the augmented reality projection device 100. In comparison with a structure in which the optical systems are separated, the coaxial optics 200 delivers light which is used for capturing an image and light which is used for project an image along optical axes which are partially identical to each other. Accordingly, image distortion is not caused and a decrease in size of the device can be achieved.

Figure 2:
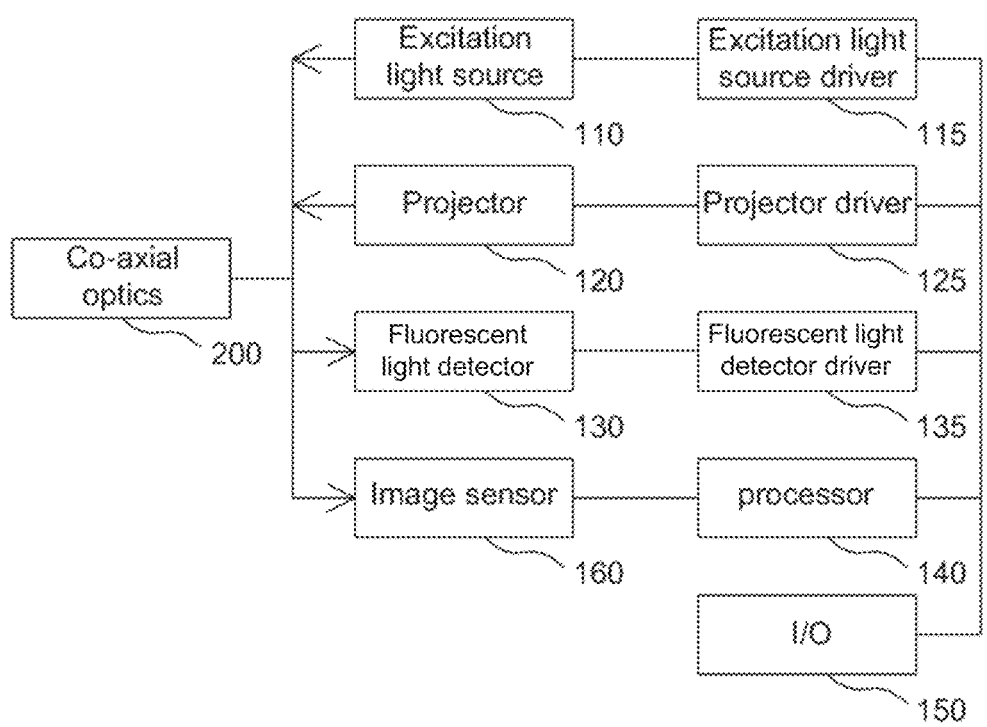
FIG. 2 is a block diagram functionally illustrating the augmented reality projection device illustrated in FIG. 1.

FIG. 2 is a block diagram functionally illustrating the augmented reality projection device illustrated in FIG. 1.

Referring to FIG. 2, the augmented reality projection device 100 can generate light and output to the outside via the coaxial optics 200, and can receive light from the outside via the coaxial optics 200. An excitation light source 110 outputs excitation light, a projector 120 outputs visual indicator light, and a fluorescent light detector 130 detects fluorescent light which is input from the outside. Additionally, the augmented reality projection device 100 may further include an image sensor 160 that detects visible light which is input from the outside.

The excitation light source 110 generates light of a wavelength band which excites a fluorescent material administered in a human body. The excitation light source 110 can generate light of, for example, about 400 nm or about 850 nm to about 800 nm. The excitation light source 110 is controlled by an excitation light source driver 115. The excitation light source driver 115 can control the excitation light source 110, for example, on the basis of operation parameters such as brightness (or intensity), an output time, and an output period of excitation light. The excitation light source driver 115 may be a light emitting diode driver that is driven with a DC voltage or an AC voltage.

The projector 120 outputs a visual indicator on the basis of an input image signal. An image signal is a digital or analog signal indicating a shape, a color, a position, and the like of a visual indicator and may be, for example, a composite or component signal. The projector 120 may be, for example, a digital light processing (DLP) projector or an LCD projector. In one embodiment, the color of a visual indicator which is generated by the projector 120 may be a monochromatic color such as blue or green. In another embodiment, the color of a visual indicator which is generated by the projector 120 may be a polychromatic color. The projector 120 is controlled by a projector driver 125. The projector driver 125 can control the projector 120 on the basis of preset operation parameters.

The fluorescent light detector 130 detects fluorescent light which is generated from the fluorescent material. The fluorescent light detector 130 includes a pixel array that detects light of a wavelength band to which fluorescent light belongs. A pixel generates an electrical signal indicating whether fluorescent light has been detected and/or brightness of fluorescent light. A fluorescent image is generated using electrical signals output from the fluorescent light detector 130. The fluorescent light detector 130 includes a readout IC (ROIC) that scans the pixels and outputs electrical signals to the outside. The fluorescent light detector 130 is controlled by a fluorescent light detector driver 135. The fluorescent light detector driver 135 controls the fluorescent light detector 130 such that the fluorescent light detector 130 can generate electrical signals by resetting and selecting the pixel array on the basis of the preset operation parameters. The resolution of the fluorescent light detector 130 can be equal to or less than the resolution of the projector 120 and/or the image sensor 160.

One or more processors 140 control the excitation light source 110, the projector 120, and the fluorescent light detector 130 via the excitation light source driver 115, the projector driver 125, and the fluorescent light detector driver 135. In one embodiment, the processor 140 can control operations of the constituent units and generate an image signal. For example, a single process may perform control of the constituent units and generation of an image signal, or one of two or more processors may control the operations of the constituent units and the other processor may generate an image signal. The processor 140 can identify a fluorescent light generation area in a fluorescent image. The processor 140 generates an image signal in which a visual indicator is displayed in the identified fluorescent light generation area. In another embodiment, the processor 140 may control the operations of the constituent units and transmit a fluorescent image to an external processing device (not illustrated) via the I/O interface 150. The external processing device can identify a fluorescent light generation area in the fluorescent image and transmit an image signal for displaying a visual indicator or area information for identifying the fluorescent light generation area, for example, coordinate values, to the processor 140 via the I/O interface 150. In case of an image signal, the projector 120 can directly receive and output the image signal. In case of area information, the processor 140 can generate an image signal for outputting a visual indicator on the basis of the area information and transmit the generated image signal to the projector 120.

The I/O interface 150 transmits and receives analog and/or digital signals between the augmented reality projection device 100 and an external device. The I/O interface 150 can transmit and receive signals to and from the external device by wired and/or wireless communication. The I/O interface 150 can support various wired/wireless communication modes such as wireless LAN which is a short-range wireless communication mode, Bluetooth which is a short-range wireless communication mode, Zigbee, Wifi-Direct, NFC, LAN which is a wired communication mode, and USB.

In addition, the augmented reality projection device 100 can further include an image sensor 160. The image sensor 160 can detect light which is incident via the coaxial optics 200 and generate a polychromatic signal. Light which is detected by the image sensor 160 may be light of a visible band which is reflected by a fluorescent light generation area and a peripheral area thereof. When a visual indicator is displayed, the image sensor 160 can also detect light which is reflected by the visual indicator. A polychromatic signal which is generated by the image sensor 160 can be output to the outside via the I/O interface 150.

Figure 3:
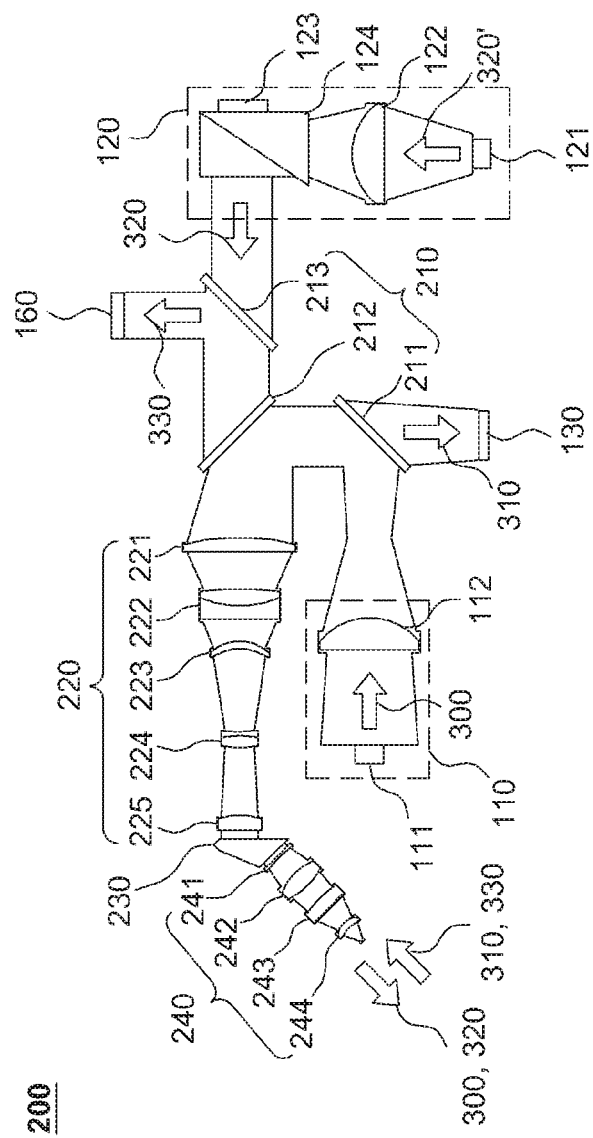
FIG. 3 illustrates a coaxial optics of the augmented reality projection device illustrated in FIG. 2.

FIG. 3 illustrates a coaxial optics of the augmented reality projection device illustrated in FIG. 2.

Referring to FIG. 3, the coaxial optics 200 includes an optical path branching/merging unit 210, a relay optics 220, a half pentaprism 230, and an objective optics 240. The relay optics 220, the half pentaprism 230, and the objective optics 240 are optical paths through which light passes commonly in the augmented reality projection device 100.

The excitation light source 110, the projector 120, and the fluorescent light detector 130 are disposed around the optical path branching/merging unit 210. The excitation light source 110 can include a light source 111 that emits excitation light 300 and a plano-convex lens 112 that refracts and collimates excitation light 300 which progresses obliquely. The projector 120 can include a light source 121 that emits visible light 320', a plano-convex lens 122 that refracts and collimates visible light 320' which progresses obliquely, a digital micromirror device (DMD) 123 that generates visual indicator light 320 using collimated visible light 320', and an internal total reflection prism 124 that reflects collimated visible light 320' to the DMD 123 and transmits visual indicator light 320.

The optical path branching/merging unit 210 includes first and second dichroic mirrors 211 and 212. The first and second dichroic mirrors 211 and 212 can be disposed substantially perpendicular to the length direction. As illustrated in FIG. 3, the first dichroic mirror 211 reflects most of excitation light 300 and transmits most of fluorescent light. For this purpose, the first dichroic mirror 211 is disposed oblique between the excitation light source 110 and the fluorescent light detector 130 which are disposed substantially perpendicular to each other when seen in the direction of progress of light. That is, the first dichroic mirror 211 can be disposed oblique by about 45 degrees at a position at which excitation light 300 and fluorescent light 310 intersect each other. The second dichroic mirror 212 reflects most of excitation light 300 and fluorescent light 310 and transmits most of visible light 320. For this purpose, the second dichroic mirror 212 can be disposed oblique between the fluorescent light detector 130 and the projector 120 which are disposed substantially perpendicular to each other when seen in the direction of progress of light. That is, the second dichroic mirror 212 can be disposed oblique by about 45 degrees at a position at which fluorescent light 310 and visual indicator light 320 intersect each other. Accordingly, excitation light 300 is reflected by the first dichroic mirror 211 such that the direction of progress direction of progress thereof is changed by about 90 degrees, is reflected by the second dichroic mirror 212 such that the direction of progress is changed by about 90 degrees, and is then incident on the relay optics 220. Fluorescent light 310 exiting from the relay optics 220 is reflected by the second dichroic mirror 212 such that the direction of progress thereof is changed by about 90 degrees, passes through the first dichroic mirror 211, and reaches the fluorescent light detector 130. On the other hand, visual indicator light 320 exciting from the projector 120 passes through the second dichroic mirror 212 and is incident on the relay optics 220. In one embodiment, the positions of the excitation light source 110 and the fluorescent light detector 130 can be replaced with each other. That is, the excitation light 300 is reflected once by about 90 degrees is incident on the relay optics 220, and fluorescent light 310 is reflected twice by about 90 degrees and reaches the fluorescent light detector 130. For this purpose, the first dichroic mirror 211 transmits excitation light 300 but reflects fluorescent light 310.

In one embodiment, the optical path branching/merging unit 210 can further include a third dichroic mirror 213. The third dichroic mirror 213 can be disposed between the second dichroic mirror 212 and the projector 120 to be substantially parallel to the first dichroic mirror 211. The third dichroic mirror 213 transmits most of visible light, that is, visible light of a specific wavelength band and reflects most of visible light other than the transmission band. Visual indicator light 320 exciting from the projector 120 is transmitted by the third dichroic mirror 213 and the second dichroic mirror 212 is then incident on the relay optics 220. Visible light 330 exciting from the relay optics 220 is reflected by the third dichroic mirror 213 such that the direction of progress thereof is changed by about 90 degrees and is then incident on the image sensor 160. Visual indicator light 320 includes light of a specific wavelength band which is transmitted by the third dichroic mirror 213 and may be monochromatic light or polychromatic light with a wavelength band broader than the specific wavelength band.

The relay optics 220 is telecentric. The relay optics 220 extends the optical paths of excitation light 300, fluorescent light 310, and visual indicator light 320 such that the excitation light source 110, the projector 120, and the fluorescent light detector 130 are efficiently arranged in a small space. The relay optics 220 delivers excitation light 300 and visual indicator light 320 which are generated in the co-axial optics to the outside via the half pentaprism 230 and the objective optics 240, and delivers fluorescent light 310 and/or visible light 330 which are incident from the outside and transmitted by the objective optics 240 and the half pentaprism 230 to the fluorescent light detector 130 and/or the image sensor 160.

The relay optics 220 reduces a numerical aperture (NA) of light progressing from the inside to the outside of the optics (light progressing leftward in FIG. 3) and enlarges NA of light progressing from the inside to the outside of the optics (light progressing rightward). The relay optics 220 includes a convex lens 221, a first chromatic aberration correcting lens 222, a convex-concave lens 223, a second chromatic aberration correcting lens 224, and a plano-convex lens 225.

The convex lens 221 is disposed such that a first convex face is directed to right (or the second dichroic mirror 212) and a second convex face is directed to left (or the half pentaprism 230). Here, the radius of curvature of the second convex face may be greater several tens times than the radius of curvature of the first convex face. On the other hand, the effective diameters $\Phi_e$ of the first convex face and the second convex face can be substantially the same. The convex lens 221 refracts light progressing leftward to the focus and refracts and collimates light progressing obliquely rightward.

The first chromatic aberration correcting lens 222 has a configuration in which crow glass is disposed on the right side and flint glass is disposed on the left side. Here, the radius of curvature of the right convex face of the crown glass is about two times the radius of curvature of the left convex face, and the radius of curvature of the left concave face of the flint glass is several tens times the radius of curvature of the right concave face. On the other hand, the effective diameters $\Phi_e$ of the convex face and the concave face can be substantially the same and can be less than the effective diameter of the convex lens 221. The first chromatic aberration correcting lens 222 can differently refract light progressing leftward depending on the wavelengths thereof but condense the light on a focus and can decrease an angel between light progressing rightward and the optical axis.

The convex-concave lens 223 is disposed such that a convex face is directed to right and a concave face is directed to left. Here, the radius of curvature of the convex face may be about 0.8 to 0.9 times the radius of curvature of the concave face. On the other hand, the effective diameter $\Phi_e$ of the convex face is greater than the effective diameter $\Phi_e$ of the concave face, and the effective diameter $\Phi_e$ of the convex face is less than the effective diameter of the first chromatic aberration correcting lens 222. The convex-concave lens 223 corrects spherical aberration of light processing leftward and increases an angle between light progressing rightward and the optical axis.

The second chromatic aberration correcting lens 224 has a configuration in which flint glass is directed to right and crown glass is directed to left. Here, the radius of curvature of the right convex face of the crown glass is about 1.2 to 1.3 times the radius of curvature of the left convex face, and the radius of curvature of the right concave face of the flint glass is about 1.1 to 1.2 times the radius of curvature of the left concave face. On the other hand, the effective diameters $\Phi_e$ of the convex face can be 1.3 to 1.4 times the effective diameter $\Phi_e$ of the concave face, and the effective diameter $\Phi_e$ of the convex face can be less than the effective diameter of the concave face of the convex-concave lens 223. The second chromatic aberration correcting lens 224 can increase an angel between light progressing leftward and the optical axis and can differently refract light progressing rightward depending on the wavelengths thereof but condense the light on a focus.

The plano-convex lens 225 is disposed such that a convex face is directed to right and a plane is directed to left. Here, the effective diameters $\Phi_e$ of the convex face and the plane can be substantially the same, and the effective diameter $\Phi_e$ of the convex face can be greater than the effective diameter of the convex face of the first chromatic aberration correcting lens 222. The plano-convex lens 225 can refract and collimate light progressing oblique leftward and obliquely refract light progressing rightward to the focus.

The half pentaprism 230 refracts an optical path obliquely by a predetermined angle. The direction of progress of excitation light 300 and visual indicator light 320 is inclined downward from the optical axis of the coaxial optics 200 due to the half pentaprism 230. The augmented reality projection device 100 can be manufactured in a small size, for example, such that an operator can use it with a hand. When the direction of progress of excitation light 300 and visual indicator light 320 is substantially parallel to the optical axis of the coaxial optics 200, an operator has to keep the hand gripping the augmented reality projection device 100 in a turned state for a considerable time. On the other hand, when the direction of progress of excitation light 300 and visual indicator light 320 is oblique with respect to the optical axis of the coaxial optics 200, an operator can allow excitation light 300 to progress to a fluorescent light generation area in a state in which the operator naturally grips the augmented reality projection device 100.

The half pentaprism 230 can be disposed between the relay optics 220 and the objective optics 240. For example, the half pentaprism 230 can be disposed between the plano-convex lens 225 of the relay optics 220 and the plano-concave lens 241 of the objective optics 240. With respect to the optical axis of the relay optics 220, the right face of the half pentaprism 230 is a plane perpendicular to the optical axis, the left face thereof is a plane inclined by a positive angle from the optical axis, a bottom surface thereof is a plane inclined by a negative angle. The right face of the half pentaprism 230 faces the relay optics 220 and the bottom face thereof faces the objective optics 240. Light incident substantially perpendicularly on the right face of the half pentaprism 230 is first reflected toward the right face by the left face, is second reflected by the right face, and progresses to the bottom surface. The direction of progress of second-reflected light can be substantially perpendicular to the bottom face of the half pentaprism 230.

The objective optics 240 is telecentric. The objective optics 240 outputs excitation light 300 and visual indicator light 320 to the outside and receives fluorescent light 310 and/or visible light 330 from the outside. The objective optics 240 can include a plano-concave lens 241, a first convex lens 242, a second convex lens 243, and a convex-concave lens 244.

The plano-concave lens 241 is disposed such that the plane is directed right-upward (or the half pentaprism 230) and the concave face is directed left-downward (or the half pentaprism 230). Here, the effective diameter $\Phi_e$ of the concave face is 0.8 to 0.9 times the effective diameter $\Phi_e$ of the plane. The plano-concave lens 241 refracts light progressing left-downward to increase an angle between the light and the optical axis of the objective optics 240 and refracts light progressing right-upward to be substantially parallel to the optical axis of the objective optics 240.

The first convex lens 242 and the second convex lens 243 are disposed such that a first convex face is directed right-upward and a second convex face is directed left-downward. Here, the radius of curvature of the second convex face of the first convex lens 242 is 1.6 to 1.7 times the radius of curvature of the first convex face, and the radius of curvature of the second convex face of the second convex lens 243 is 3.1 to 3.2 times the radius of curvature of the first convex face. On the other hand, the effective diameters $\Phi_e$ of the first convex face and the second convex face of the first convex lens 242 can be substantially the same and can be greater than the effective diameter of the plane and the concave face of the plano-concave lens 241, and the effective diameters $\Phi_e$ of the first convex face and the second convex face of the second convex lens 243 can be substantially the same and can be less than the effective diameter of the convex face of the first convex lens 242. The first convex lens 242 refracts light progressing left-downward to be inclined to the focus and refracts light progressing right-upward to be inclined to the focus. The second convex lens 243 refracts light progressing left-downward to be inclined to the focus and refracts light progressing right-upward to decrease the angle with respect to the optical axis of the objective optics 240.

The convex-concave lens 244 is disposed such that the convex face is directed right-upward and the concave face is directed left-downward. Here, the radius of curvature of the convex face is about 0.5 to 0.6 times the radius of curvature of the concave face. On the other hand, the effective diameter $\Phi_e$ of the convex face is greater than the effective diameter $\Phi_e$ of the concave face and the effective diameter $\Phi_e$ of the convex face is less than the effective diameter of the second convex lens 243. The convex-concave lens 244 refracts light progressing left-downward to be inclined to the focus and refracts light progressing right-upward to decrease the angle with respect to the optical axis of the objective optics 240.

The optical axes of excitation light 300, fluorescent light 310, and visual indicator light 320 are coaxial in the relay optics 220 and the objective optics 240. In comparison with a case in which optical systems are separate by light types, the coaxial optics 200 can decrease the size of the device in which the optical systems are mounted, and since detection (fluorescence) and display (a visual indicator) employ the same optics, processes for correcting an error between detection and display can be skipped or considerably reduced.

Figure 4A:
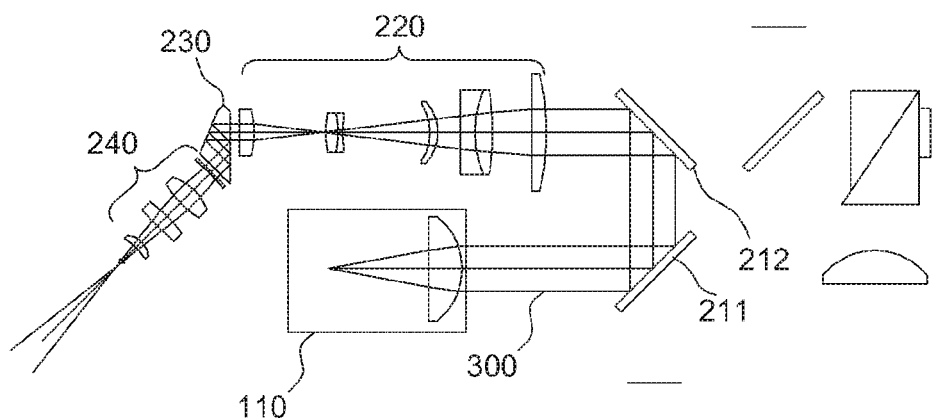
FIG. 4A illustrates an optical path of excitation light passing through the optics illustrated in FIG. 3.
Figure 4B:
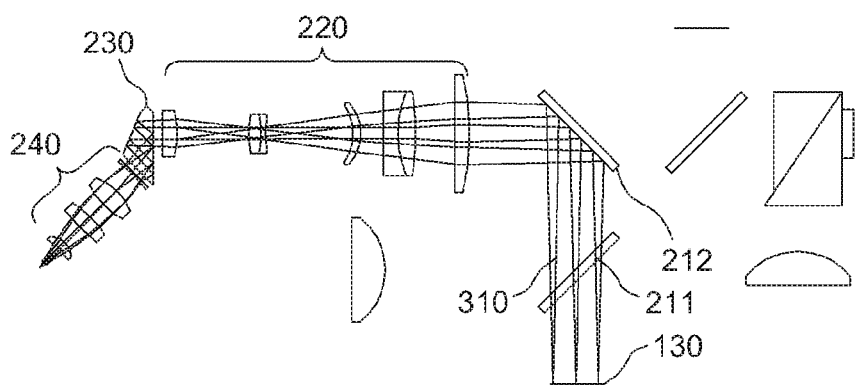
FIG. 4B illustrates an optical path of fluorescent light.

FIG. 4A illustrates an optical path of excitation light passing through the optics illustrated in FIG. 3, and FIG. 4B illustrates an optical path of fluorescent light.

Referring to FIG. 4A, most of excitation light 300 emitted from the excitation light source 110 is reflected by the first dichroic mirror 211. The excitation light 300 is refracted almost 90 degrees by the first dichroic mirror 211 and progresses upward, and most thereof is reflected by the second dichroic mirror 212. The excitation light 300 is refracted almost 90 degrees by the second dichroic mirror 212, progresses leftward, and is incident on the relay optics 220. The excitation light 300 passing through the relay optics 220 is refracted left-downward by the half pentaprism 230, and is incident on the objective optics 240. The excitation light 300 is transmitted by the objective optics 240 and is applied to a fluorescent light generation area.

Referring to FIG. 4B, the optical path of fluorescent light 310 is illustrated in consideration of NA of light. For example, NA of light incident on the fluorescent light detector 130 may be 15 to 20 times NA of light which is incident on the objective optics 240. An effective focal length between the objective optics 240 and the fluorescent light generation area, that is, a distance at which a clear fluorescent image can be acquired, is about 200 mm. Fluorescent light 310 which is generated in the fluorescent light generation area is incident on the objective optics 240. After passing through the objective optics 240, the direction of progress of fluorescent light 310 is refracted to rightward by the half pentaprism 230. After passing through relay optics 220, the fluorescent light 310 is refracted about 90 degrees by the second dichroic mirror 212 and progresses downward. After passing through the first dichroic mirror 211, the fluorescent light 310 is incident on the fluorescent light detector 130.

Figure 5A:
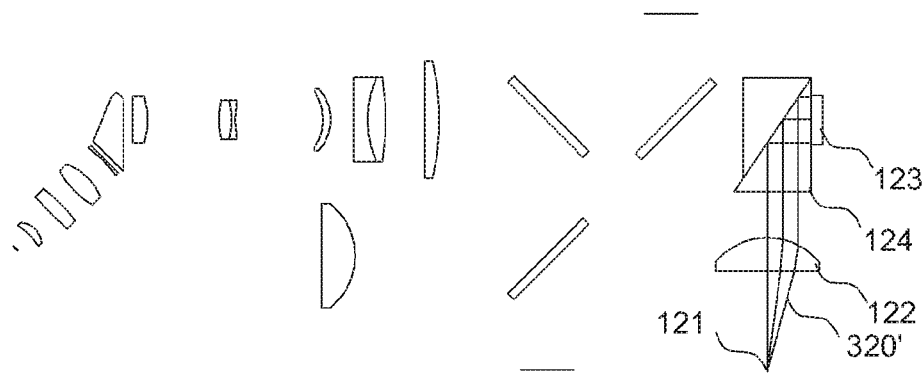
FIG. 5A illustrates optical paths in the projector.
Figure 5B:
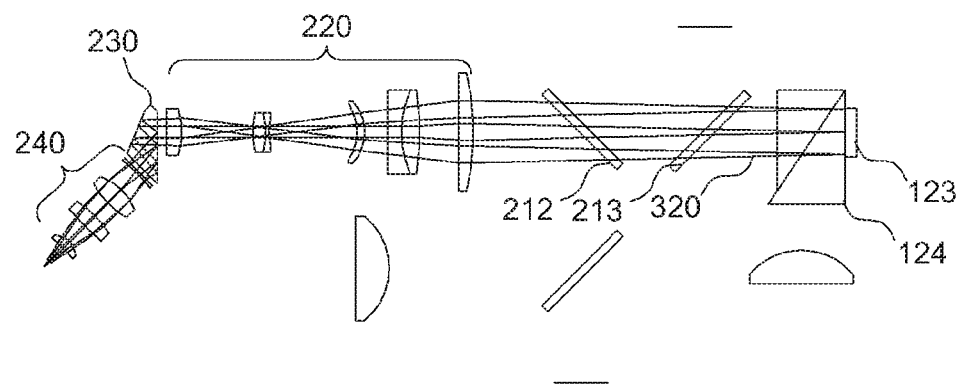
FIG. 5B illustrates visual indicator light passing through the optics illustrated in FIG. 3.
Figure 5C:
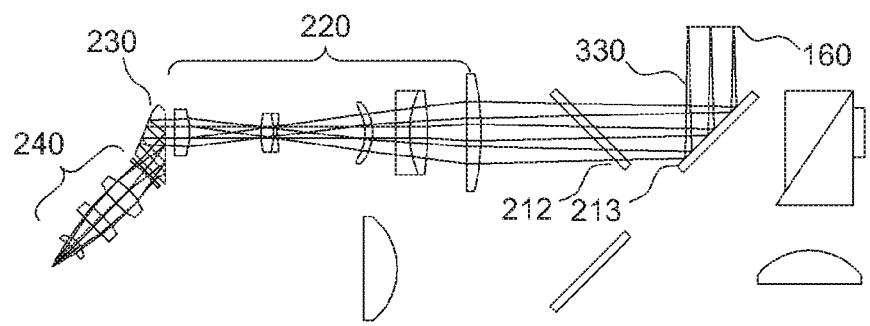
FIG. 5C illustrates optical paths of visible light.

FIG. 5A illustrates optical paths in the projector, FIG. 5B illustrates visual indicator light passing through the optics illustrated in FIG. 3, and FIG. 5C illustrates optical paths of visible light.

Referring to FIG. 5A, visible light 320' emitted from the light source 121 is incident on the DMD 123 via the plano-convex lens 122 and the internal total reflection prism 124. Here, visible light 320' and visual indicator light 320 may be monochromatic light. For example, visible light 320' and visual indicator light 320 may be light of a blue or green wavelength band.

Referring to FIG. 5B, visual indicator light 320 generated by the DMB 123 is incident on the relay optics 220 via the internal total reflection prism 124 and the second dichroic mirror 212 and/or the third dichroic mirror 213. Visual indicator light 320 passing through the relay optics 220 is refracted left-downward by the half pentaprism 230 and is incident on the objective optics 240. Visual indicator light 320 passes through the objective optics 240 and forms a visual indicator in the fluorescent light generation area.

Referring to FIG. 5C, NA of light incident on the image sensor 160 may be 15 to 20 times NA of light incident on the objective optics 240. The effective focal length between the objective optics 240 and the visual indicator may be, for example, about 200 mm. Visible light 330 indicating the fluorescent light generation area and the visual indicator displayed therein is incident on the objective optics 240. After passing through the objective optics 240, the visible light 330 is refracted rightward by the half pentaprism 230. Then, the visible light passes through the relay optics 220 and the second dichroic mirror 212. The visible light 330 is refracted almost 90 degrees by the third dichroic mirror 213, progresses upward, and is incident on the image sensor 160.

Figure 6:
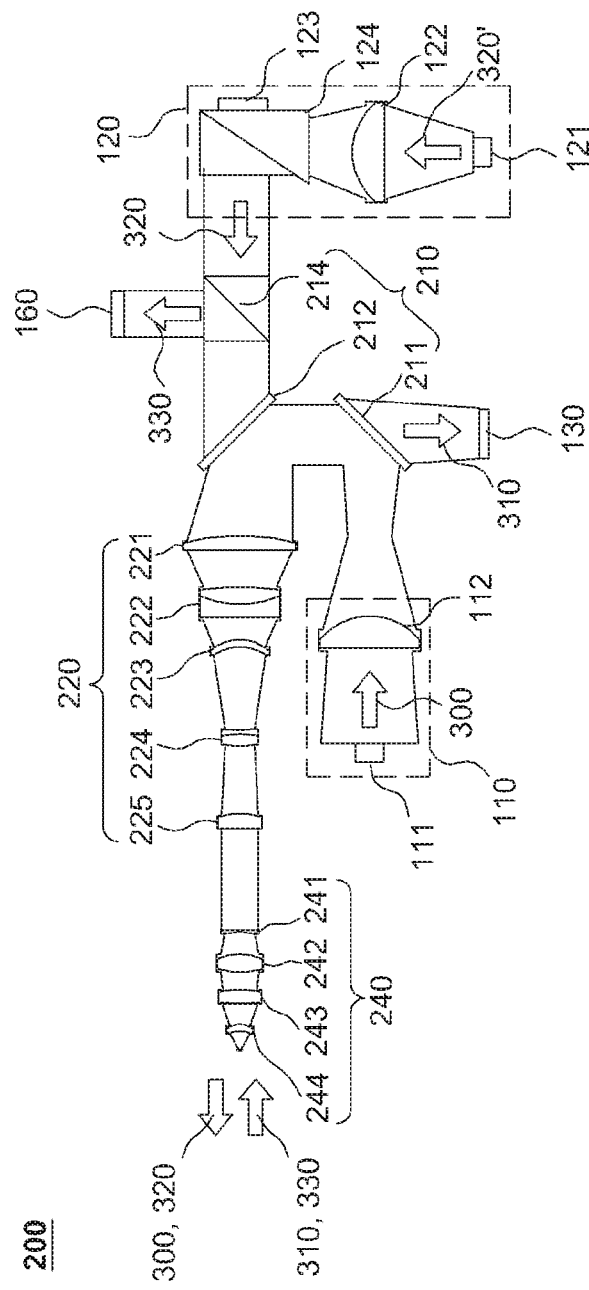
FIG. 6 illustrates another example of the coaxial optics of the augmented reality projection device illustrated in FIG. 2.
Figure 7:
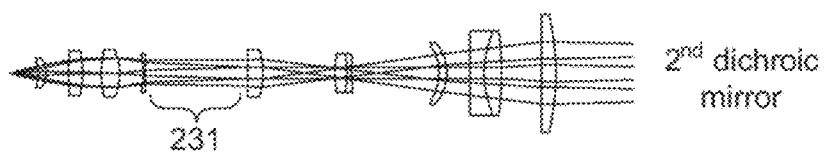
FIG. 7 illustrates optical paths in the optics illustrated in FIG. 6.

FIG. 6 illustrates another example of the coaxial optics of the augmented reality projection device illustrated in FIG. 2, and FIG. 7 illustrates optical paths in the optics illustrated in FIG. 6.

Referring to FIGS. 6 and 7, the coaxial optics 200 includes the optical path branching/merging unit 210, the relay optics 220, and the objective optics 240. The relay optics 220 and the objective optics 240 are optical paths through which light in the augmented reality projection device 100 passes commonly. The substantially same description as in FIGS. 3 to 5C will not be repeated and differences therefrom will be mainly described.

The optical path branching/merging unit 210 can be configured in combination of a dichroic mirror and a beam splitter or by only a beam splitter. For example, the optical path branching/merging unit 210 includes the first dichroic mirror 211 and the second dichroic mirror 212 and may further include a beam splitter 214. The beam splitter 214 transmits about 50% of incident light and refracts remaining 50% thereof by about 90 degrees. The beam splitter 214 is disposed between the second dichroic mirror 212 and the projector 120, transmits about 50% of visual indicator light 320 to the second dichroic mirror 212, and refracts remaining 50% thereof by about 90 degrees to the side opposite to the image sensor 160. On the other hand, the beam splitter 214 refracts about 50% of visible light 330 passing through the second dichroic mirror 212 by about 90 degrees to the image sensor 160. Here, the intensity of the visible indicator light 320 can be increased in consideration of a loss due to the beam splitter 214. The visual indicator light 320 may be monochromatic light.

The relay optics 220 and the objective optics 240 are disposed on the optical axis which is substantially horizontal. In comparison with the coaxial optics 200 illustrated in FIG. 3, the half pentaprism 230 can be replaced with an optical path 231 which extends substantially horizontally. The horizontally extending optical path 231 extends the horizontal section of the coaxial optics 200 such that the degree of freedom in arrangement of the excitation light source 110 or the projector 120 increases.

Figure 8:
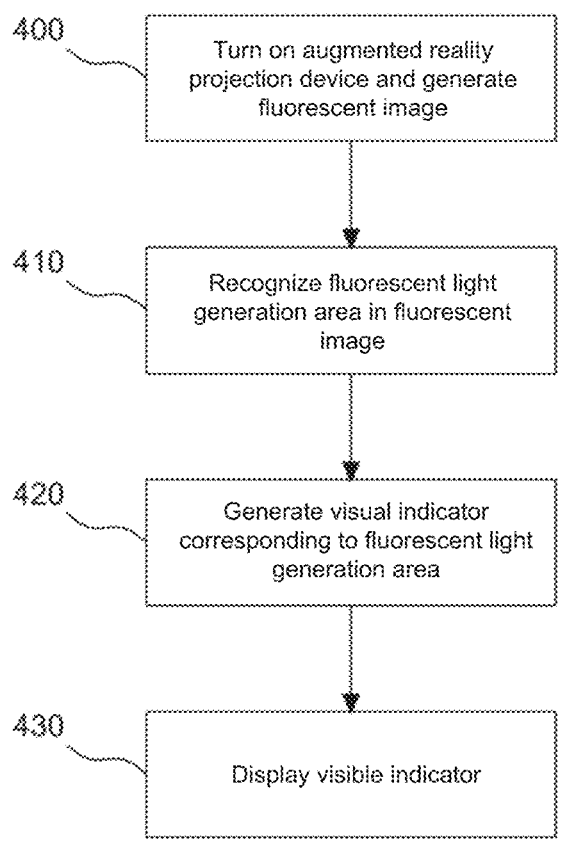
FIG. 8 is a flowchart illustrating a flow of operations of the augmented reality projection device illustrated in FIG. 1.
Figure 9:
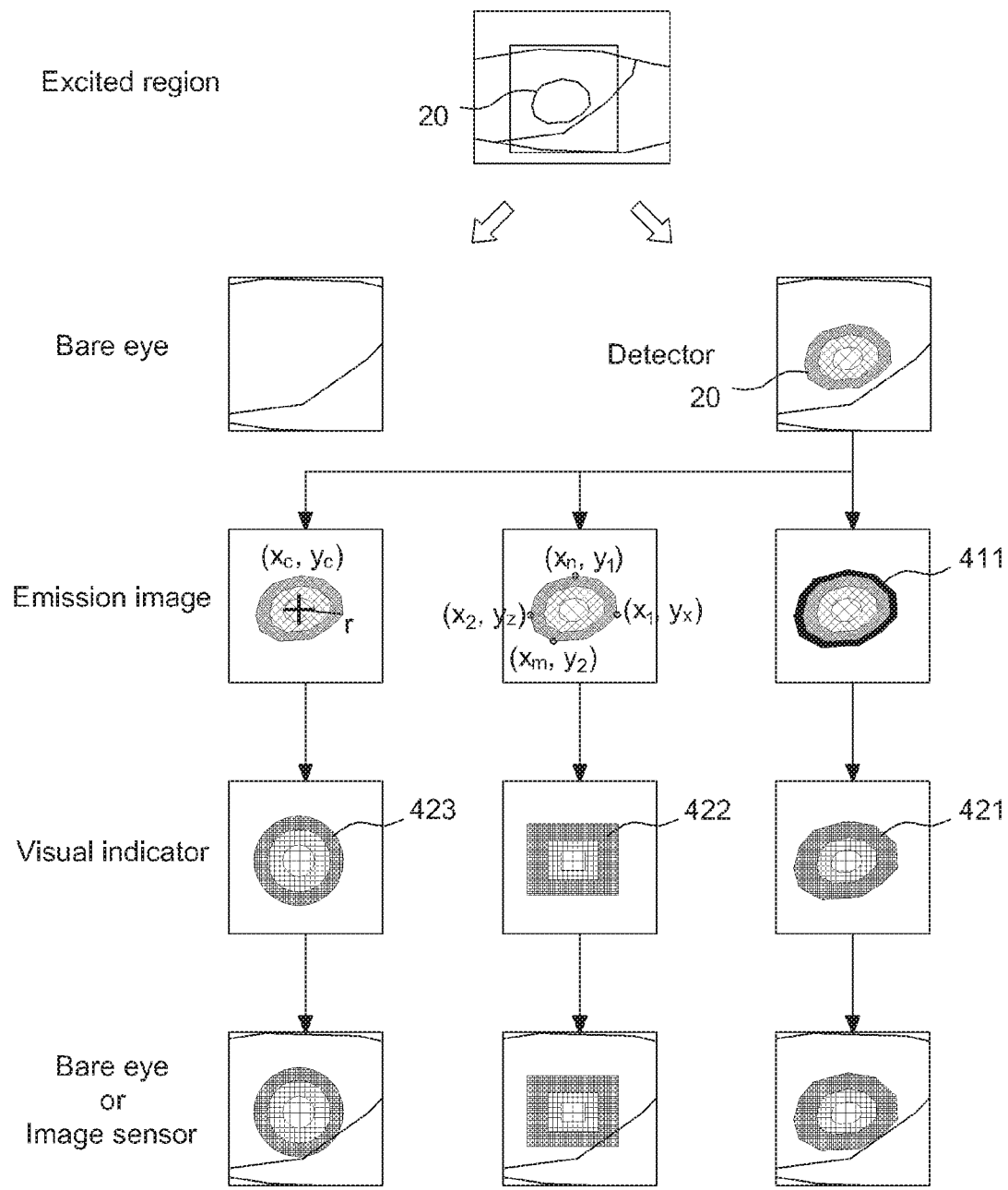
FIG. 9 illustrates an image processing procedure based on the operations illustrated in FIG. 8.

FIG. 8 is a flowchart illustrating a flow of operations of the augmented reality projection device illustrated in FIG. 1, and FIG. 9 illustrates an image processing procedure based on the operations illustrated in FIG. 8.

Referring to FIGS. 8 and 9 together, when the augmented reality projection device 100 is turned on in Step 400, a fluorescent image is generated. The processor 140 controls the excitation light source driver 115 such that the excitation light source 110 is driven. Excitation light 300 passes through the coaxial optics 200 and is applied to a dyed area 20. At the same time or within a predetermined time, the processor 140 controls the fluorescent light detector driver 135 such that the fluorescent light detector 130 is driven. Fluorescent light 310 generated in the dyed area 20 passes through the coaxial optics 200 and is incident on the fluorescent light detector 130. The fluorescent light detector 130 detects fluorescent light and generates a fluorescent image. The fluorescent image may be a still image or a moving image. In case of a still image, the fluorescent light detector 130 can generate a still image at predetermined time intervals. The resolution of a fluorescent image can be equal to or less than the resolution of a visual indicator which is displayed by visual indicator light 320. The dyed area 20 and fluorescent light generated therefrom may not be visually recognized.

In Step 410, the fluorescent light generation area is recognized in the fluorescent image. Depending on a computing capacity of the processor 140, the fluorescent light generation area may be recognized by an external processing device. Accordingly, Steps 410 and 420 may be performed by an external processing device. For example, when a fluorescent material is administered into a human body, a lesion is dyed with the fluorescent material. At this time, the peripheral of the lesion as well as the lesion can be dyed with the fluorescent material. An area dyed with the fluorescent material generates fluorescent light in response to excitation light. Brightness of fluorescent light can vary depending on a degree of dyeing, that is, an amount of fluorescent material. The dyed area 20 can include areas having different brightness of fluorescent light depending on the degree of dyeing. For example, the brightness of fluorescent light can decrease gradually as it becomes more distant from the lesion. Accordingly, pixels of a fluorescent image may have pixel values corresponding to the brightness of fluorescent light. Accordingly, the dyed area 20 and a peripheral area into which the fluorescent material is not administered can be distinguished and a difference in brightness of fluorescent light can be distinguished in the dyed area 20.

The dyed area 20 can be identified using various methods. In one embodiment, a fluorescent light detection area 411 having pixel values corresponding to fluorescent light can be converted into pixel values belonging to a visible band. As described above, the projector 120 and the fluorescent light detector 130 deliver fluorescent light and visual indicator light via the coaxial optics 200. Accordingly, a visual indicator can be enlarged, reduced, or output without any change depending on a relationship between the magnification of the projector 120 and the magnification of the fluorescent light detector 130, and thus the fluorescent light generation area 411 can be identified only through the process of converting pixel values corresponding to fluorescent light into pixel values belonging to a visible band. On the other hand, for example, a boundary of a fluorescent light detection area 411 can be identified through an outline detection algorithm. A plurality of areas can be identified in the fluorescent light detection area 411 depending on the brightness of fluorescent light. In another embodiment, a plurality of pixels having a pixel value corresponding to fluorescent light may be selected in a fluorescent image and the boundary of the fluorescent light detection area 411 may be determined. In still another embodiment, when a fluorescent image is expressed by XY coordinates, a rectangular area can be defined using the largest X coordinate value $x_1$, the smallest X coordinate value $x_2$, the largest Y coordinate value $y_1$, and the smallest Y coordinate value $y_2$. The rectangular area which is defined by coordinates $(x_1, y_1)$, $(x_2, y_1)$, $(x_1, y_2)$, and $(x_2, y_2)$ can be included in the fluorescent light detection area 411. Similarly to detection of an outline, a plurality of rectangular areas can be identified in the fluorescent light detection area 411 depending on the brightness of fluorescent light. In still another embodiment, a center of a fluorescent light detection area 411 may be determined in a fluorescent image and a circular area with a radius r which is a distance from the center to the most distant pixel may be defined. The circular area which is defined by the center coordinate $(x_1, y_1)$ and the radius r can include a fluorescent light detection area 411. Similarly to detection of an outline, a plurality of circular areas can be identified in the fluorescent light detection area 411 depending on the brightness of fluorescent light.

In Step 420, visual indicators 421, 422, 423 are generated. The visual indicators 421, 422, 423 can be generated to correspond to the area identified in Step 410. The shapes of the visual indicators 421, 422, 423 can be selected variously. In one embodiment, the processor (or an external processing device) 140 can generate an image signal for displaying a visual indicator corresponding to the boundary of the fluorescent light detection area 411. The visual indicator 421 may be a shape which matches the boundary of the fluorescent light detection area 411 or which is obtained by enlarging or reducing the fluorescent light detection area 411. In another embodiment, the processor 140 may generate a rectangular visual indicator 422 which is defined by coordinates $(x_1, y_1)$, $(x_2, y_1)$, $(x_1, y_2)$, and $(x_2, y_2)$. In still another embodiment, the processor 140 may generate a circular visual indicator 423 which is defined by the center coordinate $(x_1, y_1)$ and the radius r.

The visual indicators 421, 422, 423 can reflect the brightness of fluorescent light in a dyed area 20. In one embodiment, when the visual indicator light 320 is monochromatic light, the visual indicators 421, 422, 423 may be generated such that an area with high brightness of fluorescent light is displayed relatively bright and an area with low brightness of fluorescent light is displayed relatively dark. For example, when a fluorescent light detection area 411 is partitioned into a plurality of areas, the visual indicators 421, 422, 423 may be generated such that the areas have different brightness. For example, when a fluorescent light detection area 411 is not partitioned into a plurality of areas, the visual indicators 421, 422, 423 may be generated such that the brightness changes continuously. In another embodiment, when visual indicator light 320 is monochromatic light, the visual indicators 421, 422, 423 may be generated such that different patterns are displayed depending on the brightness of fluorescent light. For example, circles with the same size may be displayed densely in an area with high brightness of fluorescent light and circles with the same size may be displayed coarsely in an area with low brightness of fluorescent light.

In still another, when visual indicator light 320 is polychromatic light, the visual indicators 421, 422, 423 may be generated such that they are displayed in different colors depending on the brightness of fluorescent light. For example, an area with high brightness of fluorescent light may be displayed in red and an area with low brightness of fluorescent light may be displayed in yellow.

In Step 430, a visual indicator is displayed. The projector 120 converts an image signal including the visual indicator into visual indicator light 320 and applies the visual indicator light 320 to the dyed area 20 via the coaxial optics 200. The visual indicator is projected to the dyed area 20 or the periphery of the dyed area 20. Accordingly, an operator of the augmented reality projection device 100 can visually recognize the dyed area 20. On the other hand, the dyed area 20 to which the visual indicator is projected can be converted into a color signal by the image sensor 160. The color signal generated by the image sensor 160 can be transmitted to the outside and can be stored or displayed therein.

Figure 10:
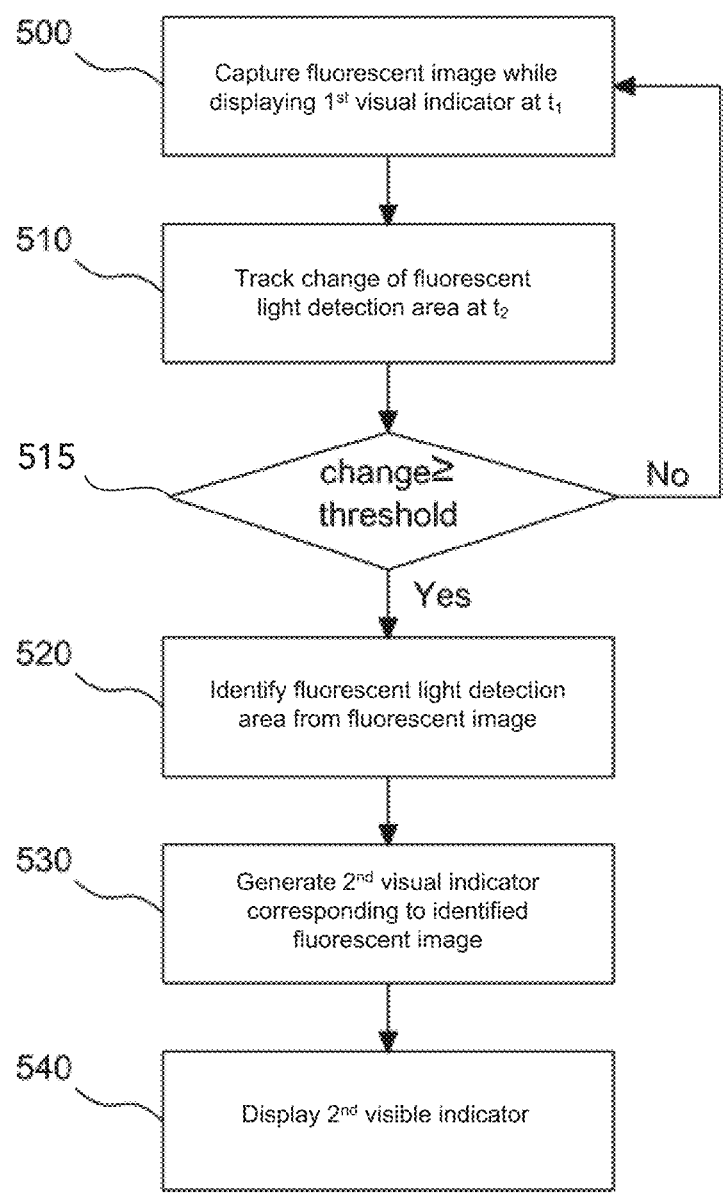
FIG. 10 is a flowchart illustrating a flow of operations of tracking change of an excited area, which is performed by augmented reality projection device 100 illustrated in FIG. 1.
Figure 11:
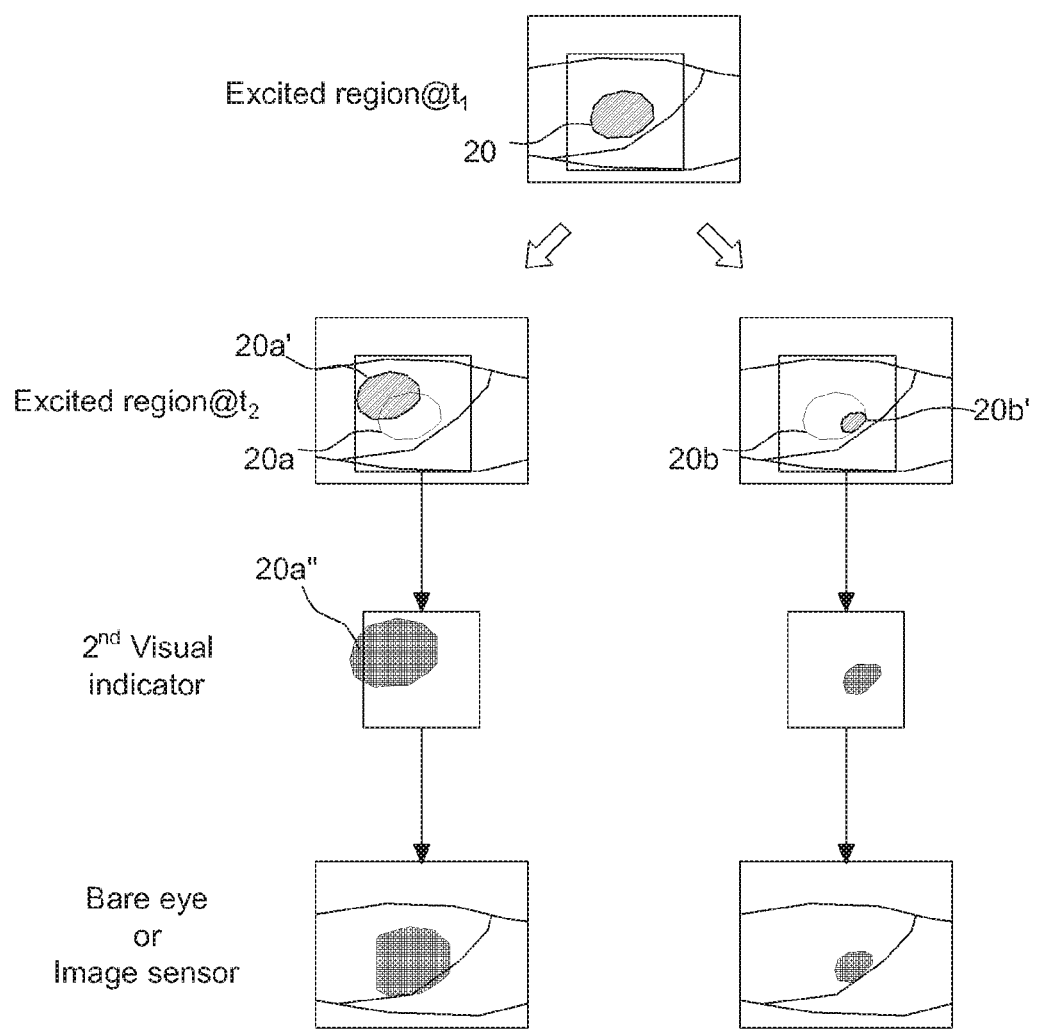
FIG. 11 illustrates an image processing procedure based on the flow of operations illustrated in FIG. 10.

FIG. 10 is a flowchart illustrating a flow of operations of tracking change of an excited area, which is performed by augmented reality projection device 100 illustrated in FIG. 1. FIG. 11 illustrates an image processing procedure based on the flow of operations illustrated in FIG. 10.

While a visual indicator is being projected, a fluorescent light detection area in a fluorescent image can be changed for various reasons. For example, when an operator moves the augmented reality projection device 100 to be horizontal, a position to which excitation light 300 is projected is changed and the position of the detected fluorescent light detection area can also be changed (a left fluorescent image in FIG. 11). For example, when an operator moves the augmented reality projection device 100 to be closer to or distant from the dyed area 20, the size and/or position of the fluorescent light detection area can be changed. For example, when a fluorescent material is administered into a human body and a part of a fluorescent light generation area is incised, the shape of the fluorescent light detection area can be changed (a right fluorescent image in FIG. 11).

In Step 500, a visual indicator generated at time $t_1$ is projected to the fluorescent light generation area and a fluorescent image is acquired. Projection of a visual indicator and acquisition of a fluorescent image are the same as described above with reference to FIGS. 6 and 7. In one embodiment, the augmented reality projection device 100 can track change of a fluorescent light generation area substantially at the same time as projecting a visual indicator. Accordingly, the augmented reality projection device 100 can track change of the size, position, and/or shape of a fluorescent light detection area in a fluorescent image and change the visual indicator almost in real time. In another embodiment, at predetermined time intervals and/or when change of the fluorescent light detection area is equal to or greater than a predetermined level, the augmented reality projection device 100 can reflect the change in the visual indicator. Accordingly, when the detected change does not affect identification of the fluorescent light generation area, the augmented reality projection device 100 may not change the visual indicator.

In Step 510, at time $t_2$, it is detected whether a fluorescent light detection area has been changed. When the projection position of excitation light 300 is changed, the position of the fluorescent light detection area 20a detected at time $t_1$ is shifted to a new position 20a' at time $t_2$. On the other hand, when at least a part of the fluorescent light generation area is removed or the augmented reality projection device 100 is separated from the area, the shape of the fluorescent light detection area 20b detected at time $t_2$ can be changed or reduced (20b'). The change of the fluorescent light detection area can be detected by comparing the images acquired at times $t_1$ and $t_2$. A difference between the two images can be calculated in various manners and a threshold value can vary depending on what manner is selected.

In Step 515, the change between two fluorescent light images is compared to a threshold value. When the change of a fluorescent image is equal to or less than the threshold value, the operation can proceed to Step 500 and the visual indicator may not be newly generated. When the change of a fluorescent image is equal to or greater than the threshold value, the operation can proceed to Step 520 and the visual indicator may be newly generated.

In Step 520, when the change of a fluorescent image is equal to or greater than the threshold value, a fluorescent light detection area is identified in the fluorescent image. In Step 530, a new visual indicator is generated from the identified fluorescent image. In Step 540, the generated visual indicator is displayed. When a part 20a'' of the fluorescent light detection area is not detected, the augmented reality projection device 100 can notify the operator, for example, using warning sound or vibration. On the other hand, when a part 20a'' of the fluorescent light detection area is not detected, the augmented reality projection device 100 may change and display the color of the visual indicator.

The above description is exemplary, and those skilled in the art can understand that the described technology can be modified in other forms without changing the technical concept or the essential feature of the described technology. Therefore, it should be understood that the above-mentioned embodiments are exemplary in all respects, but are not definitive.

The scope of the described technology is defined by the appended claims, not by the above detailed description, and it should be construed that all changes or modifications derived from the meanings and scope of the claims and equivalent concepts thereof are included in the scope of the described technology.

What is claimed is:

1. An augmented reality projection device comprising:
   an excitation light source configured to generate excitation light which is applied to a fluorescent light generation area to excite a fluorescent material;
   a fluorescent light detector configured to detect fluorescent light generated in the fluorescent light generation area and generate a fluorescent image, the fluorescent light including a fluorescent light detection area corresponding to the fluorescent light generation area;
   a projector configured to convert an image signal for displaying a visual indicator in the fluorescent light generation area into visual indicator light, the visual indicator being generated to correspond to the identified fluorescent light detection area;
   a processor configured to control operations of the excitation light source, the fluorescent light detector, and the projector; and
   a coaxial optics configured to deliver the excitation light and the visual indicator light to the fluorescent light generation area and deliver the fluorescent light to the fluorescent light detector,
   wherein the excitation light, the fluorescent light, and the visual indicator light pass through optical paths which are partially common by the coaxial optics,
   wherein the coaxial optics includes:
   an optical path branching/merging unit configured to cause an optical path of the excitation light and an optical path of the visual indicator light to be substantially identical to each other and substantially branch an optical path of the fluorescent light from the optical path of the excitation light;
   a relay optics configured to deliver the excitation light, the fluorescent light, and the visual indicator light in processing directions thereof;
   a half pentaprism horizontally coupled to the relay optics and configured to incline the optical path of the excitation light and the optical path of the visual indicator light, and cause the optical path of the fluorescent light to be horizontal; and
   an objective optics obliquely coupled to the half pentaprism and configured to deliver the excitation light and the visual indicator light emitted from the half pentaprism to the fluorescent light generation area and to deliver the fluorescent light emitted from the fluorescent light generation area to the half pentaprism.

2. The augmented reality projection device according to claim 1, wherein the optical path branching/merging unit includes:
   a first dichroic mirror that is disposed oblique at a position at which the excitation light emitted from the excitation light source and progressing horizontally and the fluorescent light progressing vertically to the fluorescent light detector intersect each other and is configured to reflect the excitation light and to transmit the fluorescent light; and
   a second dichroic mirror that is disposed oblique at a position at which the visual indicator light emitted from the projector and progressing horizontally and the excitation light reflected by the first dichroic mirror and progressing vertically intersect each other and is configured to reflect the excitation light and the fluorescent light and to transmit the visual indicator light.

3. The augmented reality projection device according to claim 2, further comprising:
   an image sensor that generates a color signal using visible light which is reflected from the fluorescent light generation area to which a visual indicator has been projected using the visual indicator light; and
   a third dichroic mirror that is disposed oblique between the second dichroic mirror and the projector and is configured to transmit the visual indicator light and to reflect the visible light,
   wherein the visible light reaches the image sensor through the coaxial optics.

4. The augmented reality projection device according to claim 3, wherein the first dichroic mirror and the third dichroic mirror are disposed to be substantially parallel to each other and the first dichroic mirror and the second dichroic mirror are disposed to be perpendicular to teach other.

5. The augmented reality projection device according to claim 3, wherein a resolution of the fluorescent light detector is equal to or less than a resolution of the image sensor.

6. The augmented reality projection device according to claim 1, wherein the optical path branching/merging unit includes:
   a first dichroic mirror that is disposed oblique at a position at which the excitation light emitted from the excitation light source and progressing horizontally and the fluorescent light progressing vertically intersect each other and is configured to transmit the excitation light and to reflect the fluorescent light; and
   a second dichroic mirror that is disposed oblique at a position at which the visual indicator light emitted from the projector and progressing horizontally and the excitation light transmitted by the first dichroic mirror intersect each other and is configured to reflect the excitation light and the fluorescent light and to transmit the visual indicator light.

7. The augmented reality projection device according to claim 1, wherein brightness of the visual indicator reflects brightness of the fluorescent light.

8. The augmented reality projection device according to claim 1, wherein the visual indicator light is monochromatic light.

9. The augmented reality projection device according to claim 1, further comprising an I/O interface that communicates with the outside,
wherein the fluorescent image is output to the outside via the I/O interface and the image signal is received from the outside via the I/O interface.

10. The augmented reality projection device according to claim 1, wherein the processor identifies the fluorescent light detection area in the fluorescent image and generates the image signal for displaying the visual indicator corresponding to the identified fluorescent light detection area.

11. The augmented reality projection device according to claim 1, wherein the fluorescent image is a still image or a moving image.

12. The augmented reality projection device according to claim 1, wherein the visual indicator changes when a difference between fluorescent images which are generated at different times is equal to or greater than a threshold value.

13. An augmented reality projection device comprising:
an excitation light source configured to generate excitation light which is applied to a fluorescent light generation area to excite a fluorescent material;
a fluorescent light detector configured to detect fluorescent light generated in the fluorescent light generation area and generate a fluorescent image, the fluorescent light including a fluorescent light detection area corresponding to the fluorescent light generation area;
a projector configured to convert an image signal for displaying a visual indicator in the fluorescent light generation area into visual indicator light, the visual indicator being generated to correspond to the identified fluorescent light detection area;
an image sensor configured to generate a color signal using visible light which is reflected from the fluorescent light generation area to which a visual indicator has been projected using the visual indicator light; and
a coaxial optics configured to deliver the excitation light and the visual indicator light to the fluorescent light generation area and deliver the fluorescent light to the fluorescent light detector,
wherein the excitation light, the fluorescent light, and the visual indicator light pass through optical paths which are partially common by the coaxial optics,
wherein the coaxial optics includes:
an optical path branching/merging unit configured to cause an optical path of the excitation light and an optical path of the visual indicator light to be substantially identical to each other and substantially branch an optical path of the fluorescent light and an optical path of the visible light from the optical path of the excitation light;
a relay optics configured to deliver the excitation light, the fluorescent light, the visual indicator light, and the visible light in processing directions thereof;
a half pentaprism horizontally coupled to the relay optics and configured to incline the optical path of the excitation light and the optical path of the visual indicator light, and cause the optical path of the fluorescent light and the optical path of the visible light to be horizontal; and
an objective optics obliquely coupled to the half pentaprism and configured to deliver the excitation light and the visual indicator light emitted from the half pentaprism to the fluorescent light generation area and to deliver the fluorescent light and the visible light emitted from the fluorescent light generation area to the half pentaprism.

14. The augmented reality projection device according to claim 13, further comprising an I/O interface that communicates with the outside,
wherein the fluorescent image is output to the outside via the I/O interface and the image signal is received from the outside via the I/O interface.

15. The augmented reality projection device according to claim 13, wherein brightness of the visual indicator reflects brightness of the fluorescent light.

16. An augmented reality projection device comprising:
an excitation light source configured to generate excitation light which is applied to a fluorescent light generation area to excite a fluorescent material;
a fluorescent light detector configured to detect fluorescent light generated in the fluorescent light generation area and generate a fluorescent image, the fluorescent light including a fluorescent light detection area corresponding to the fluorescent light generation area;
a projector configured to convert an image signal for displaying a visual indicator in the fluorescent light generation area into visual indicator light, the visual indicator being generated to correspond to the identified fluorescent light detection area;
an image sensor configured to generate a color signal using visible light which is reflected from the fluorescent light generation area to which a visual indicator has been projected using the visual indicator light; and
a coaxial optics configured to deliver the excitation light and the visual indicator light to the fluorescent light generation area and deliver the fluorescent light to the fluorescent light detector, wherein the excitation light, the fluorescent light, and the visual indicator light pass through optical paths which are partially common by the coaxial optics,
wherein the coaxial optics includes an optical path branching/merging unit configured to cause an optical path of the excitation light and an optical path of the visual indicator light to be substantially identical to each other and substantially branch an optical path of the fluorescent light and an optical path of the visible light from the optical path of the excitation light, and
wherein the optical path branching/merging unit includes:
a first dichroic mirror that is disposed oblique at a position at which the excitation light emitted from the excitation light source and progressing horizontally and the fluorescent light progressing vertically to the fluorescent light detector intersect each other and is configured to reflect the excitation light and to transmit the fluorescent light;
a second dichroic mirror that is disposed oblique at a position at which the visual indicator light emitted from the projector and progressing horizontally and the excitation light reflected by the first dichroic mirror and progressing vertically intersect each other and is configured to reflect the excitation light and the fluorescent light and to transmit the visual indicator light; and a third dichroic mirror that is disposed oblique between the second dichroic mirror and the projector and is configured to transmit the visual indicator light and to reflect the visible light.

\* \* \* \* \*